United States Patent
Benoit et al.

(10) Patent No.: US 9,333,181 B2
(45) Date of Patent: May 10, 2016

(54) METHOD FOR PREPARING FUNCTIONALIZED LIPID CAPSULES

(75) Inventors: Jean-Pierre Benoit, Angers (FR); Thomas Perrier, Angers (FR)

(73) Assignees: UNIVERSITE D'ANGERS, Angers (FR); INSTITUT NATIONAL DE LA SANTE ET DE LA RECHERCHE MEDICALE, Paris (FR)

( * ) Notice: Subject to any disclaimer, the term of this patent is extended or adjusted under 35 U.S.C. 154(b) by 1198 days.

(21) Appl. No.: 13/260,168

(22) PCT Filed: Mar. 30, 2010

(86) PCT No.: PCT/IB2010/051377
§ 371 (c)(1),
(2), (4) Date: Feb. 28, 2012

(87) PCT Pub. No.: WO2010/113111
PCT Pub. Date: Oct. 7, 2010

(65) Prior Publication Data
US 2012/0148669 A1    Jun. 14, 2012

(30) Foreign Application Priority Data
Mar. 31, 2009    (FR) ...................................... 09 52048

(51) Int. Cl.
| | |
|---|---|
| *A61K 9/20* | (2006.01) |
| *A61K 9/51* | (2006.01) |
| *A23L 1/00* | (2006.01) |
| *A23L 1/30* | (2006.01) |
| *A61K 8/11* | (2006.01) |
| *A61K 8/60* | (2006.01) |
| *A61K 8/64* | (2006.01) |
| *A61K 47/48* | (2006.01) |
| *A61Q 19/00* | (2006.01) |

(52) U.S. Cl.
CPC ............. *A61K 9/5123* (2013.01); *A23L 1/0032* (2013.01); *A23L 1/30* (2013.01); *A61K 8/11* (2013.01); *A61K 8/606* (2013.01); *A61K 8/64* (2013.01); *A61K 47/48869* (2013.01); *A61Q 19/00* (2013.01); *A61K 2800/413* (2013.01); *A61K 2800/612* (2013.01); *Y10T 428/2984* (2015.01)

(58) Field of Classification Search
CPC ..... A61K 9/51; A61K 9/5107; A61K 9/5138; A61K 9/5146; A61K 9/5161; A61K 9/5123; A61K 9/5192

USPC .................................................. 424/464–489
See application file for complete search history.

(56) References Cited

U.S. PATENT DOCUMENTS

| | | | |
|---|---|---|---|
| 5,635,609 | A | 6/1997 | Levy et al. |
| 6,087,003 | A | 7/2000 | Benoit et al. |
| 2003/0152635 | A1 | 8/2003 | Heurtault et al. |
| 2005/0214803 | A1* | 9/2005 | Wang ................................ 435/6 |
| 2007/0140965 | A1 | 6/2007 | Lanza et al. |
| 2007/0184076 | A1 | 8/2007 | Unger et al. |
| 2008/0160094 | A1 | 7/2008 | Nelson et al. |
| 2008/0253960 | A1 | 10/2008 | Zheng et al. |
| 2009/0035223 | A1 | 2/2009 | Chen et al. |
| 2009/0238865 | A1 | 9/2009 | Heurtault et al. |
| 2010/0233275 | A1 | 9/2010 | Saulnier et al. |
| 2010/0266676 | A1 | 10/2010 | Saulnier et al. |

FOREIGN PATENT DOCUMENTS

| | | |
|---|---|---|
| EP | 0 547 191 B1 | 12/1996 |
| EP | 1 666 486 A1 | 6/2006 |
| EP | 1955695 A1 * | 8/2008 |
| FR | 2 677 272 | 12/1992 |
| JP | 06-500795 A | 1/1994 |
| JP | 2003-525257 A | 8/2003 |
| WO | WO 92/21330 A1 | 12/1992 |
| WO | 01 64328 | 9/2001 |
| WO | WO 2005/023844 A1 | 3/2005 |
| WO | 2007 106683 | 9/2007 |

OTHER PUBLICATIONS

International Search Report Issued Jun. 22, 2010 in PCT/IB10/051377 Filed Mar. 30, 2010.
French Search Report Issued Nov. 13, 2009 in French Patent Application No. 0952048 Filed Mar. 31, 2009.
U.S. Appl. No. 13/139,401, filed Jun. 13, 2011, Benoit, et al.

* cited by examiner

*Primary Examiner* — Johann R Richter
*Assistant Examiner* — Micah-Paul Young
(74) *Attorney, Agent, or Firm* — Oblon, McClelland, Maier & Neustadt, L.L.P.

(57) ABSTRACT

The present invention relates to a liquid lipid core/solid lipid shell capsule surface-functionalized with at least one compound containing at least one amino function, characterized in that the lipid core/lipid shell architecture is on the nanometric scale and in that said compound is covalently bonded to said solid lipid shell via a transacylation reaction. It also relates to a method for preparing such capsules.

23 Claims, 4 Drawing Sheets

METHOD FOR PREPARING FUNCTIONALIZED LIPID CAPSULES

Figure 1:
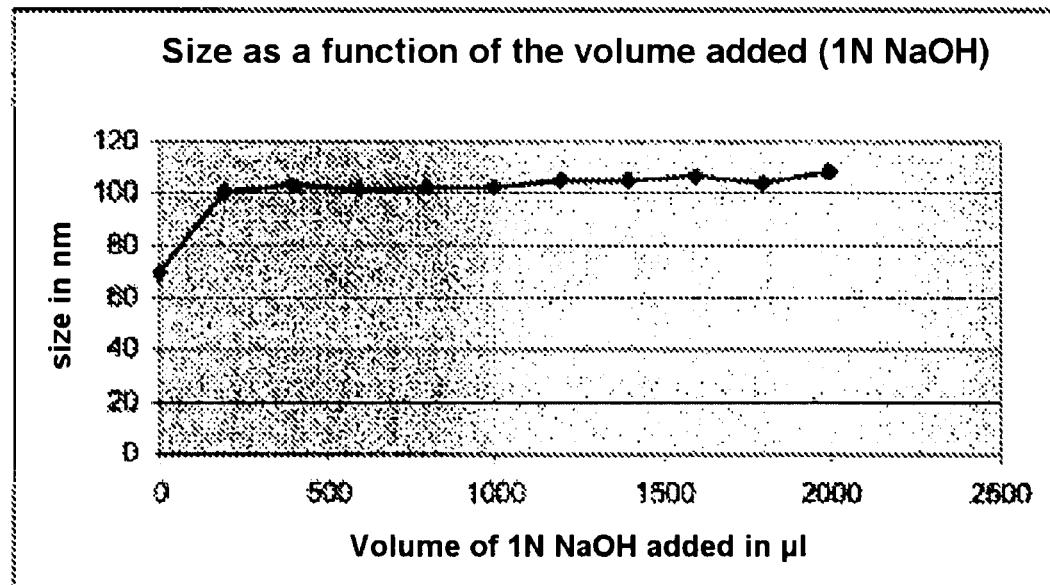

The present invention aims to propose novel vesicular systems, in particular of capsules comprising a solid lipid envelope and a liquid lipid core.

Nanocapsule or nanodroplet systems of which the size ranges from 50 to 500 nanometers and which are made up of a liquid or semi-solid core, covered with an external membrane, are already known.

For example, U.S. Pat. No. 5,961,970 proposes, as a vehicle for active agents, oil-in-water emulsions on the submicronic scale, i.e. miniemulsions, the droplets of which have a hydrophobic core of lipid nature and are surface-stabilized with amphiphilic and/or nonionic surfactants like phospholipid surfactants. U.S. Pat. No. 5,576,016 describes macroemulsions of which the droplets are made up of a solid lipid core and which are stabilized with a phospholipid envelope. EP 1 265 698, WO 09/001,019 and FR 2 916 974, for their part, describe nanocapsules comprising a liquid core and solid shell of lipid nature, that can be obtained from a microemulsion prepared by the technique of phase inversion via a thermal effect (PIT emulsion).

These nanoparticulate systems are mostly dedicated to the encapsulation of an active agent which, depending on its nature, which may be hydrophilic, hydrophobic or water-dispersible, will be present in the core and/or in the shell.

For the purpose of the present invention, the expression "encapsulation of an active agent" is intended to mean its incorporation into the core or the shell of a nanocapsule, according to its nature, which may be hydrophilic, hydrophobic or water-dispersible.

However, these vesicular systems do not simultaneously lend themselves to the transport of a large variety of active agents and/or to a total control of their releasing and/or targeting capacity. Indeed, these systems allow the encapsulation only of relatively low molecular weight active agents, in particular of molecular weight less than or equal to approximately 5 000 daltons. Moreover, it would be advantageous to be able to reinforce the capsule structure of these nanocapsules in order to prevent, for example, any untimely release of the active agent that they transport or else to increase the resistance of their envelope to aggressive biological media like, for example, gastric juices. It could also be particularly advantageous to be able to readily surface-functionalize them with a view, for example, to dedicating them to a specific target. Thus, it could be particularly advantageous to take advantage of ligands of galactose type in order to direct these nanocapsules to the receptor expressed by hepatocytes, or of arginine-glycine-aspartate RGD peptide type in order to target the $\alpha V \beta 3$ integrins expressed by certain highly vascularized tumors.

The invention aims specifically to propose a method of functionalizing these vesicular systems which makes it possible to confer the abovementioned advantages thereon.

Unexpectedly, the inventors have noted that the external surface of nanocapsules can lend itself to such a functionalization provided that said functionalization is carried out under specific conditions.

Against all expectations, the surface-functionalization of these nanocapsules does not affect their stability and does not lead to their disaggregation, as confirmed in the examples hereinafter by the dynamic light scattering measurements or by the transmission electron microscopy imaging.

Thus, according to a first of its aspects, the present invention is directed toward a liquid lipid core/solid lipid shell capsule surface-functionalized with at least one compound containing at least one amine function, characterized in that the lipid core/lipid shell architecture is on the nanometric scale and in that said compound is covalently bonded to said solid lipid shell via a transacylation reaction.

According to another of its aspects, the present invention is directed toward a method that is of use for the functionalization of nanoparticles comprising a solid lipid shell and a liquid lipid core, said method comprising at least the steps consisting in:
i) providing nanocapsules comprising a solid lipid shell and a liquid lipid core,
ii) bringing said nanocapsules into contact with an alkaline aqueous solution, so as to activate their surface for a transacylation reaction,
iii) bringing the medium ii) into contact with at least one compound containing at least one amine function so as to form, by transacylation, said expected capsules and, where appropriate,
(iv) neutralizing the resulting functionalized capsules, and
(v) isolating said functionalized capsules.

Admittedly, EP 0 693 963 describes the preparation of particles of which the shell is said to be "gelled", from esterified polysaccharides, present in the shell of the particle under consideration, and capable of reacting with a polyamine via a transacylation reaction.

However, besides their nature that is very different from those under consideration according to the invention, the starting particles which undergo a transacylation reaction have a size ranging from a few micrometers to 10 millimeters.

It so happens that particles of smaller size, in particular on the nanometric scale, advantageously have a high colloidal stability. The nanoparticles thus functionalized withstand flocculation or aggregation and have a longer lifetime.

For the purpose of the present invention, the term "functionalized nanocapsules" is intended to mean nanocapsules comprising a solid lipid shell, the surface of which has a modified structure compared with the surface of the nanocapsules in a nonfunctionalized state, this modified structure being in particular the result of surface-grafting of at least one or more compounds bearing at least one amine function.

For the purposes of simplification, these compounds can also be hereinafter denoted amino compounds. Such compounds can advantageously have at least two, at least three, or even more, amine functions.

It is easy to understand that the anchoring of such molecules gives the nanocapsule thus functionalized a greater size than its initial (i.e. nonfunctionalized) size. Thus, if the initial nanocapsules have an average size of less than 150 nm, preferably less than 100 nm, more preferably less than 50 nm, the capsules obtained following their functionalisation can, for their part, have an average size of greater than 150 nm, or even than 200 nm. The control of the process, and in particular of the reaction time, makes it possible to control the final size of the functionalized nanocapsules, which advantageously can remain less than 250 nm.

The amino compound attached to the surface of the capsules according to the invention can also be suitable for the attachment of one or more molecules of interest.

Thus, for the purpose of the invention, the term "amino compound" covers either an active agent as such, also termed molecule of interest, i.e. an entity having a biological, pharmacological, cosmetic or phytosanitary activity, or a chemical or biological entity capable of conferring one or more supplementary functionalities on the nanocapsules, and in particular capable of reinforcing their external structure and/ or of allowing a specific targeting of the associated active agent(s).

Advantageously, the amino compound and/or the molecule of interest is (are) of protein, peptide, nucleic, polymeric or inorganic nature, or even organometallic nature.

From the viewpoint of the nanocapsules under consideration, a method according to the invention proves to be most particularly advantageous for:
- reinforcing their nanocapsular structure,
- modifying their encapsulated active ingredient release kinetics, where appropriate,
- increasing their resistance to aggressive biological media such as the digestive tract,
- protecting the oily core containing one or more active agent(s) against any external attack (oxidation, light),
- taking advantage of these nanoparticles for transporting high-molecular-weight molecules or hydrophilic polymers capable of reacting after transacylation, such as nucleic acids, siRNAs, heparins and heparin derivatives, negatively or positively charged proteins and polypeptides, or macropolyanions, and/or
- allowing the presentation, at the surface of these nanoparticles, of molecules that interact with the immune system.

According to another of its subjects, the present invention is also directed toward the use of capsules according to the invention for preparing compositions.

Thus, the invention relates to the use of at least one capsule according to the invention for preparing a composition of therapeutic, cosmetic or nutraceutical interest.

The present invention is therefore also directed toward compositions, in particular pharmaceutical compositions, containing at least one capsule according to the invention in combination with at least one physiologically acceptable vehicle.

Capsules

In the subsequent text, the term "LNC" signifies "lipid nanocapsules".

As indicated above, the capsules according to the invention in fact correspond to nanocapsules comprising a solid lipid shell and a liquid lipid core, which are surface-functionalized via a transacylation process.

The resulting capsules have an average size of between 70 and 250 nm. Of course, capsules of larger size can be obtained by appropriately varying the parameters of the process.

Such variations are of course within the scope of those skilled in the art.

Such capsules can be analyzed by dynamic light scattering and small angle neutron scattering.

As indicated above, the external shell of the capsules comprises at least one amino compound covalently grafted at its surface via a transacylation reaction.

According to the present invention, the terms "bonded" and "grafted" are used without distinction to denote the establishing of a covalent bond between the shell and the amino compound, this bond deriving from a transacylation reaction established between the two entities.

According to a first variant, this amino compound is, in itself, a molecule of interest, as described above, that it is advantageous to transport via a capsule in accordance with the invention.

As specified above, this molecule of interest may be of protein, peptide, nucleic or polymeric nature.

It may in particular be a protein, preferably chosen from hydrophilic proteins or proteins treated so as to be made hydrophilic, i.e. water-soluble or water-dispersible, containing free amino groups, polypeptides or polymers.

Examples of proteins which can be used in the invention and which meet the requirements that consist in being hydrophilic or else which can be treated so as to be hydrophilic, are albumins, such as serum albumin, in particular human serum albumin, ovalbumin or alpha-lactalbumin, globulins, fibrinogen, casein, plant proteins such as soya or wheat proteins, glutenins which will preferably have been degraded, solubilized scleroproteins, collagen, atelocollagen, gelatin, gelatin hydrolysates, peptones, hemoglobin, enzymes such as catalase or alkaline phosphatase, hormones, immunoglobulins or antibodies such as monoclonal anti-bodies.

Advantageously, as examples of a polypeptide, mention may be made of poly(aspartic acid), polyarginine or else polylysine.

By way of example of a polymer, mention may be made of synthetic polymers, and more particularly polyethyleneimine (PEI).

By way of example of a nucleic acid, mention may more particularly be made of siRNA.

According to a second variant which can, where appropriate, be inherent in the first variant, the amino compound is used to transport an ancillary active agent more particularly considered from the viewpoint of its targeting and/or labeling capacity. When the amino compound is more particularly considered for these purposes, i.e. as an agent that must bond a molecule of interest to nanocapsules, the choice of amino compounds chosen from monoclonal antibodies, RGD ligands, amino sugars and polylysine may more particularly be preferred.

With regard to the molecule of interest represented by the active agent, it may be in accordance with the definition proposed above for the amino compound.

It may also be, for example, a substance of interest for diagnosis, bearing, for example, fluorescent, luminescent or phosphorescent entities, or else a molecule having a biological activity, such as an enzyme, a hormone, an antibody or hemoglobin.

According to yet another variant, the amino compound is of interest from the viewpoint of its ability to reinforce the nanocapsular external surface resistance. It may thus be any molecule comprising polyethylene glycol units. A surface coating based on such a compound is in fact advantageous for conferring increased vascular persistence owing to a significant reduction in the uptake of the nanocapsules by hepatic macrophages.

According to yet another embodiment, the capsules according to the invention are also advantageous with regard to the fact that they can have, at their external surface, a certain number of reactive ancillary units, for instance amine and acid units suitable for coupling to ancillary entities. Such units are advantageously present on the amino compound having been used to functionalize the nanocapsules. Thus, according to yet another embodiment variant, the amino compounds under consideration according to the invention can have the significant advantage of conferring on the initial nanocapsules an ability to associate, via their amine units attached by trans-acylation to the surface of these nanocapsules, with other molecule(s) that is (are) of interest in terms of therapeutic effect, of labeling, of targeting and/or of protection against any possible degradation caused by the surrounding medium.

The molecules of interest, capable of being noncovalently bonded to an amino compound, itself grafted at the surface of the lipid shell of the capsule, can be either an active agent, in particular a hydrophilic active agent, which is more particularly negatively charged, or a molecule dedicated to providing the nanocapsule with an ancillary functionality, in particular in terms of targeting/labeling or for the purposes of reinforcing the resistance and stability of the nanocapsule.

The active agent may be a compound of therapeutic interest, which is in particular pharmaceutically active, cosmetically active or active in a phyto-sanitary or food or nutraceutical field.

According to one preferred embodiment, this active agent is a pharmaceutically active ingredient, as defined above.

The nanocapsules of the invention are more particularly suitable for the administration of the following active ingredients: anti-infectives among which are antimycotics; antibiotics; anticancer agents; immuno-suppressants; active ingredients intended for the central nervous system which must pass the blood-brain barrier, such as antiparkinsonians, analgesics and more generally active ingredients for treating neuro-degenerative diseases.

Advantageously, such an active agent may be of protein, polypeptide or peptide nature, but may also be a nucleic acid such as a DNA plasmid or an interfering RNA (or siRNA), or an antisense oligonucleotide or an aptamer. Where appropriate, the capsules functionalized with an active agent, bonded to the lipid shell directly or via an ancillary amino compound, can undergo an additional treatment aimed at functionalizing their external surface with an ancillary compound, for instance a polylysine, in order to reinforce the protection of the active agent attached.

The capsules thus formed can be likened to a multilayer system.

Such an embodiment variant is illustrated in example 9.

As indicated above, the capsules according to the invention comprise a solid lipid shell.

Solid Lipid Shell

This lipid shell is solid and comprises at least one compound capable of reacting with an amino compound via a transacylation reaction. It is generally a compound comprising at least one ester function.

This compound bearing the ester function may be a compound that contributes in parallel to the formation and the constitution of the solid lipid shell, such as, for example, a lipophilic surfactant, or even an ancillary compound, introduced into the lipid shell only for the purposes of establishing transacylation reactions.

Thus, the solid lipid shell comprises at least one liposoluble or lipophilic surfactant.

Advantageously, the lipophilic surfactant is solid at ambient temperature.

The lipophilic surfactant is more particularly based on phosphoplipids which are advantageous from the viewpoint of their biocompatible nature.

Among the phospholipids, phosphatidylcholines (lecithins) are most particularly advantageous.

Other phospholipids may be phosphatidylglycerol, phosphatidylinositol, phosphatidylserine, phosphatidic acid and phosphatidylethanolamine.

The phospholipid derivatives may be isolated from natural sources or prepared by synthesis.

By way of commercial products deriving from phospholipids, mention may more particularly be made of:

EPICURON 120® (Lukas Meyer, Germany) which is a mixture of approximately 70% of phosphatidylcholine, 12% of phosphatidylethanolamine and approximately 15% of other phospholipids;

OVOTINE 160® (Lukas Meyer, Germany) which is a mixture comprising approximately 60% of phosphatidylcholine, 18% of phosphatidylethanolamine and 12% of other phospholipids;

a mixture of purified phospholipids like the products Lipoid E75® or Lipoid E-80® (Lipoid, Germany) which is a mixture of phospholipids comprising approximately 80% by weight of phosphatidylcholine, 8% by weight of phosphatidylethanolamine, 3.6% by weight of nonpolar lipids and 2% of sphingomyelin.

According to one preferred embodiment, the lipophilic surfactant is a lecithin of which the proportion of phosphatidylcholine ranges from 40 to 80% by weight.

Lipoid S75-3® (Lipoid GmbH, Germany) is most particularly suitable as a source of phosphatidycholine. It is soya lecithin. The latter contains approximately 69% of phosphatidylcholine and 9% of phosphatidylethanolamine. This constituent is the only constituent that is solid at 37° C. and at ambient temperature in the formulation. Polyglyceryl-6-dioleate (Plurol®) can also be used.

Advantageously, the abovementioned surfactant(s) can be combined with cosurfactants such as, for example, other phospholipids. In this respect, phosphatidylcholines (lecithins) are particularly advantageous.

Other phospholipids suitable for the invention may be phosphatidylglycerol, phosphatidylinositol, phosphatidylserine, phosphatidic acid and phosphatidylethanolamine.

Advantageously, according to one embodiment variant, the solid lipid shell is made up of at least one surfactant system comprising a liposoluble surfactant as defined above and a nonionic hydrophilic thermosensitive surfactant.

Advantageously, a nonionic hydrophilic thermosensitive surfactant is an ampiphilic hydrophilic surfactant.

The emulsifying surfactants normally used have an HLB (HLB=hydrophilic lipophilic balance) ranging from 8 to 18.

These surfactants can be chosen from ethoxylated fatty alcohols, ethoxylated fatty acids, partial glycerides of ethoxylated fatty acids, polyethoxylated fatty acid triglycerides, and mixtures thereof.

As ethoxylated fatty alcohols, mention may, for example, be made of the products of addition of ethylene oxide with lauryl alcohol, in particular those comprising from 9 to 50 oxyethylene groups (laureth-9 to laureth-50 in CTFA names); the products of addition of ethylene oxide with behenyl alcohol, in particular those comprising from 9 to 50 oxyethylene groups (beheneth-9 to beheneth-50 in CTFA names); the products of addition of ethylene oxide with cetostearyl alcohol (mixture of cetyl alcohol and of stearyl alcohol), in particular those comprising from 9 to 30 oxythylene groups (ceteareth-9 to ceteareth-30 in CTFA names); the products of addition of ethylene oxide with cetyl alcohol, in particular those comprising from 9 to 30 oxyethylene groups (ceteth-9 to ceteth-30 in CTFA names); the products of addition of ethylene oxide with stearyl alcohol, in particular those comprising from 9 to 30 oxyethylene groups (steareth-9 to steareth-30 in CTFA names); the products of addition of ethylene oxide with isostearyl alcohol, in particular those comprising from 9 to 50 oxyethylene groups (isosteareth-9 to isosteareth-50 in CTFA names); and mixtures thereof.

As ethoxylated fatty acids, mention may, for example, be made of the products of addition of ethylene oxide with lauric acid, palmitic acid, stearic acid or behenic acid, and mixtures thereof, in particular those comprising from 9 to 50 oxyethylene groups, such as the laurates of PEG-9 to PEG-50 (in CTFA names: PEG-9 laurate to PEG-50 laurate); the palmitates of PEG-9 to PEG-50 (in CTFA names: PEG-9 palmitate to PEG-50 palmitate); the stearates of PEG-9 to PEG-50 (in CTFA names: PEG-9 stearate to PEG-50 stearate); the palmito-stearates of PEG-9 to PEG-50; the behenates of PEG-9 to PEG-50 (in CTFA names: PEG-9 behenate to PEG-50 behenate); and mixtures thereof.

Mixtures of these oxyethylenated derivatives of fatty alcohols and of fatty acids may also be used.

These surfactants can also be either natural compounds like the phospholipids or synthetic compounds, such as polysorbates which are polyethoxylated sorbitol fatty acid esters (Tween®), esters of polyethylene glycol and of a fatty acid originating, for example, from castor oil (Cremophor®), polyethoxylated fatty acids, for example stearic acid (Simulsol M-53®), polyoxyethylenated fatty alcohol ethers (Brij®), poly-oxyethylenated nonphenyl ethers (Triton N®), or poly-oxyethylenated hydroxyphenyl ethers (Triton X®).

It may more particularly be a polyethylene glycol 2-hydroxystearate, and in particular the product sold under the name Solutol® HS15 by the company BASF (Germany).

According to one preferred embodiment, the shell contains at least one surfactant system made up of a lecithin and a polyethylene glycol 2-hydroxystearate and in particular the product sold under the name Solutol® HS15.

According to a first embodiment variant, at least one abovementioned surfactant is, provided that it has an ester function, involved, moreover, in at least one transacylation reaction under consideration according to the invention.

According to a second embodiment variant, the lipid shell comprises, in addition to at least one of the abovementioned surfactants, at least one alcohol ester distinct from said surfactants, present so as to provide at least one transacylation reaction required according to the invention.

Advantageously, the carbon number of said alcohol ester is an integer less than or equal to 12, more particularly less than or equal to 10, even more particularly less than or equal to 8.

Such esters are illustrated in example 6.

Among the alcohol esters suitable for the present invention, the ester corresponding to the following formula is particularly advantageous:

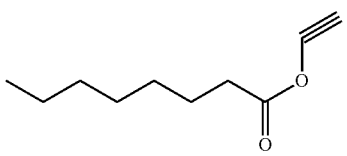

Incorporation of these esters into a formulation of lipid nanocapsules according to the invention can be carried out in a proportion by weight of about from 1 to 25% by weight and more particularly from 5 to 20% by weight, relative to the total weight of the mixture of surfactant(s) and of esters under consideration for the formation of the lipid shell.

In general, capsules in accordance with the invention can contain about from 1 to 10% by weight of alcohol esters distinct from the surfactants that they otherwise contain, relative to their total weight, taking into account only the inorganic substances of the formulation.

The use of an alcohol ester according to the present invention makes it possible to significantly reinforce the stability of the initial properties of the LNCs, in particular in terms of their colloidal stability and their stealth. Another advantage, conferred by the use of such alcohol esters as sites for the transacylation reaction at the level of the lipid shell of the capsules according to the present invention, is based on their great accessibility to the reactants that can potentially be used during this transacylation step, with as a result an improvement in the attachment yield, as can be seen in the examples.

Of course, the abovementioned two transacylation reaction embodiment variants can coexist in one capsule according to the invention provided of course that the shell of said capsule contains, in addition to the surfactants, in particular lipophilic surfactants, at least one alcohol ester as defined above.

The shell can, where appropriate, also encapsulate at least one active agent. In this case, it will rather be an active agent of liposoluble or lipodispersible nature.

Advantageously, such liposoluble or lipodispersible active agents are already present in the starting nanocapsules, used in step i) of the preparation method according to the invention.

According to one embodiment, the solid lipid shell is devoid of proteins.

The capsules according to the present invention comprise, moreover, a liquid lipid core.

Liquid Lipid Core

The liquid lipid core comprises at least one oily fatty phase made up of at least one liquid or semi-liquid fatty substance, and in particular of at least one triglyceride, of a fatty acid ester, or of a mixture thereof.

The fatty acid ester may be more particularly chosen from $C_8$ to $C_{18}$, in particular $C_8$ to $C_{12}$, fatty acid esters, and in particular ethyl palmitate, ethyl oleate, ethyl myristate, isopropyl myristate, octyldodecyl myristate and mixtures thereof.

The triglycerides used may be synthetic triglycerides or triglycerides of natural origin. The natural sources may include animal fats or vegetable oils, for example soya oils, or long-chain triglyceride (LCT) sources.

Other triglycerides of interest are composed mainly of medium-length fatty acids, also called medium-chain triglycerides (MCT). A medium-chain triglyceride (MCT) oil is a triglyceride in which the carbohydrate chain contains from 8 to 12 carbon atoms.

Such MCT oils are commercially available.

By way of example of these MCT oils, mention may be made of the TCR products (tradename from the Société Industrielle Des Oléagineux, France, for a triglyceride mixture in which approximately 95% of the fatty acid chains contain 8 or 10 carbon atoms) and Miglyol® 812 (triglyceride sold by the company Dynamit Nobel, Sweden, for a mixture of caprylic and capric acid glyceride triesters).

The fatty acid units of these triglycerides may be unsaturated, monounsaturated or polyunsaturated. Mixtures of triglycerides containing varying fatty acid units are also acceptable.

The HLB value, or hydrophilic-lipophilic balance, is as defined by C. Larpent in Traité K.342 of the Editions Techniques de l'Ingénieur.

The triglyceride sold under the name Labrafac WL 1349® is most particularly suitable for the invention.

In one preferred embodiment, the fatty phase is a fatty acid triglyceride.

As indicated above, the liquid lipid core can, where appropriate, encapsulate an active agent within it. This active agent is preferably liposoluble. However, active agents of water-soluble or water-dispersible nature can also be encapsulated in the lipid core. In this case, it will have to undergo a formulation prior to its encapsulation.

For example, the active agent may be in the form of reverse micelles or microemulsions, as is, for example, described in documents WO 09/001,019 and FR 2 916 974, respectively.

By way of nonlimiting illustration of active agents that can be encapsulated according to the invention, mention may in particular be made of doxorubicin and addition salts thereof with a pharmaceutically acceptable acid, and more particularly the hydrochloride, and low-molecular-weight heparins.

Method for Preparing Capsules According to the Invention

As indicated above, capsules in the nanoparticulate state undergo a transacylation reaction between at least one constituent of their solid lipid envelope and at least one amino compound.

This transacylation reaction corresponds to a reaction in which acyl group(s) is(are) exchanged between a compound of the lipid envelope, preferably a surfactant, in particular a liposoluble surfactant, or an alcohol ester, if present, as described above, and the amino compound under consideration.

According to one preferred embodiment variant, said liposoluble surfactant is a lecithin.

Advantageously, such a reaction is simple to carry out and does not require any difficult handling.

The first step of this reaction consists of an alkalinisation of the surface of the nanocapsules so as to activate them, with respect to a transacylation reaction, for example, by contact of these nanocapsules with at least one alkaline aqueous solution.

Advantageously, the amount of alkaline agent to be added to the aqueous phase in which the nanocapsules are directly dispersed, in order to initiate the trans-acylation reaction, is such that the pH of the aqueous suspension of nanocapsules is between 8 and 14, and more preferably between 8 and 10.

The alkaline agent to be added in order to initiate the transacylation reaction can be, for example, chosen from sodium hydroxide, potassium hydroxide or an amino compound such as, for example, triethylamine.

The second step of this reaction consists in bringing these alkalinized nanocapsules into contact with at least one amino compound under conditions suitable for the transacylation. The reaction is preferably left to stir for the amount of time necessary for the reaction to take place, i.e. between 5 minutes and 30 minutes.

For example, the time for which the particles are kept in the alkaline solution in order for the transacylation reaction to develop can be between 5 min and 1 hour, preferably between 5 min and 30 min, more preferably it is 15 min.

Said amino compound used in the transacylation reaction functionalizing the nanocapsules according to the present invention is advantageously as defined above.

The yield from the transacylation reaction can be increased by increasing the duration of said trans-acylation reaction and/or by variations in the composition of the alkaline solution initiating said transacylation reaction, and in particular by increasing the amount of alkaline agent used to prepare said alkaline solution.

Advantageously, at the end of the transacylation, a final step of neutralizing the reaction medium is carried out by adding a solution of hydrochloric acid of suitable concentration, generally between 0.1 mol/liter and 6 mol/liter, the pH having to be brought back to a value of between 7 and 7.4.

The acidic agent used to neutralize the aqueous suspension of particles after the transacylation reaction can, for example, be chosen from monocarboxylic or polycarboxylic organic acids optionally bearing alcohol functions, such as acetic acid, citric acid, tartaric acid, succinic acid, malic acid, or lactic acid, or an inorganic acid such as hydrochloric acid or sulfuric acid.

This particle neutralization time, i.e. the stirring time necessary after addition of the acid to the reaction medium, can be between 5 min and 1 hour, preferably between 5 min and 30 min, more preferably it is 15 min.

The modified nanocapsules can subsequently be purified according to purification methods well known to those skilled in the art, such as the dialysis or filtration technique or chromatographic techniques (HPLC for example, ion exchange column, size exclusion separation).

Method for Preparing the Starting Nanocapsules

For the purpose of the invention, the term "nanocapsules" is to be distinguished from nanospheres. The term "nanocapsules" is intended to mean particles consisting of a core that is liquid or semi-liquid at ambient temperature, coated with a film or shell that is solid at ambient temperature, as opposed to nanospheres which are matrix particles, i.e. the entire mass of which is solid. Thus, when nanospheres contain a pharmaceutically active ingredient, said ingredient is finely dispersed in the solid matrix.

Advantageously, the nanocapsules of step i) of the method according to the invention, i.e. the nanocapsules in a nonfunctionalized state, i.e. not having undergone any transacylation, have an average size of less than 150 nm, preferably less than 100 nm, more preferably less than 50 nm. These sizes can be determined by photon correlation spectroscopy, scanning electron microscopy or transmission electron microscopy in cryoscopic mode.

The thickness of the solid film or shell is advantageously between 2 and 10 nm. It is approximately equal to one tenth of the diameter of the particles. This thickness can be calculated via the mass balance, or visualized by negative-shadow transmission electron microscopy or alternatively by transmission electron microscopy in cryoscopic mode or by small angle neutron scattering.

Given their size, the starting nanocapsules are colloidal lipid particles.

The polydispersity index of the nanocapsules of the invention is advantageously between 5 and 15%. This index is determined on the size histogram obtained by the photon correlation spectroscopy method.

The nanocapsules each consist of an essentially lipid core that is liquid or semi-liquid at ambient temperature, coated with an essentially lipid shell that is solid at ambient temperature.

For the purpose of the invention, the expression "essentially lipid" means that the core and the shell forming the nanocapsules according to the invention consist of more than 50% by weight, in particular more than 75% by weight, especially more than 80% by weight, or even more than 90%, more particularly more than 95% of their respective weights, or even totally, of one or more lipid (hydrophobic) compounds. These percentages are assessed by considering that the surfactants which are present form part of the liquid phase.

For the purpose of the invention, the expression "ambient temperature" denotes a temperature ranging from 18 to 25° C.

The starting nanocapsules can advantageously be obtained according to a method comprising at least the steps consisting in:

a) providing a microemulsion formulated by phase inversion of an emulsion and stabilized with at least one surfactant system containing at least one liposoluble surfactant as defined above, b) quenching said microemulsion so as to obtain nanocapsules made up of a lipid core that is liquid at ambient temperature and coated with a lipid film that is solid at ambient temperature.

A microemulsion that is most particularly suitable for the formation of starting nanocapsules comprises at least one oily fatty phase, one aqueous phase and one surfactant system comprising at least one lipophilic surfactant, as defined above, and preferably also a nonionic hydrophilic thermosensitive surfactant, and, where appropriate, at least one alcohol ester, the carbon number of which is preferentially an integer of less than or equal to 12, more particularly less than or equal to 10, even more preferentially less than or equal to 8.

Such a microemulsion can, for example, be prepared in the following way.

All of the constituents intended to form the microemulsion are weighed into a container. The mixture is homogenized, for example by means of a Rayneri mixer at 350 rpm, and heated by gradually increasing the temperature, by means of a water-bath, to a temperature greater than or equal to the phase inversion temperature $T_2$, i.e. until a more viscous white phase is obtained, which indicates that the inverse emulsion has been obtained. The heating is then stopped and the stirring is maintained until ambient temperature is again reached, passing through the phase inversion temperature $T_1$, i.e. the temperature at which the expected microemulsion forms, in the form of a transparent or translucent phase. It should be noted that, when the temperature has come back down below the phase inversion temperature ($T_1$) zone, the starting emulsion is again obtained. This succession of operations is advantageously repeated and, when the temperature is again at the phase inversion temperature $T_1$, cooling is performed in order to form the expected nanocapsules.

Such a technique is more particularly described in the abovementioned documents FR 2 916 974 and EP 1 265 698.

When it is desired to encapsulate an active agent in particular of lipophilic nature within the lipid core, such starting nanocapsules can be obtained according to a similar method of preparation, comprising two additional steps between the abovementioned steps a) and b), consisting in:
  providing a second composition, distinct from said microemulsion and totally or partly made up of at least one active agent,
  bringing said microemulsion into contact with said second composition under conditions suitable for the interaction of said active agent with said microemulsion.

Such a method is more particularly detailed in FR 2 916 974.

Alternatively, such starting nanocapsules encapsulating an active agent can be prepared according to a method of preparation comprising at least the steps consisting in:
  providing at least one first microemulsion of water-in-oil nature, stabilized with at least one lipophilic surfactant as defined above and containing, in its hydrophilic phase, at least one active agent, in particular of hydrophilic or water-dispersible nature as defined above,
  providing at least one second microemulsion, distinct from the first microemulsion, formulated by phase inversion of an emulsion and stabilized with at least one nonionic hydrophilic thermosensitive surfactant as defined above,
  adding said first microemulsion to said second microemulsion, under conditions suitable for the formation of a new microemulsion internalizing said active agent in its hydrophilic phase, and
  quenching said microemulsion obtained in the preceding step, so as to obtain the expected nanocapsules.

According to one embodiment variant, at least one of the microemulsions, and preferably the first, also contains at least one alcohol ester distinct from the surfactants.

The present invention is illustrated by the following examples and figures which are given by way of non-limiting illustration of the field of the invention.

FIGURES

FIG. 1: Change in the size (in nm) of the nanocapsules obtained according to the preparation method of the invention, as a function of the volume of NaOH (1N) added (in µl), in the presence of a constant amount of human serum albumin.

Figure 2:
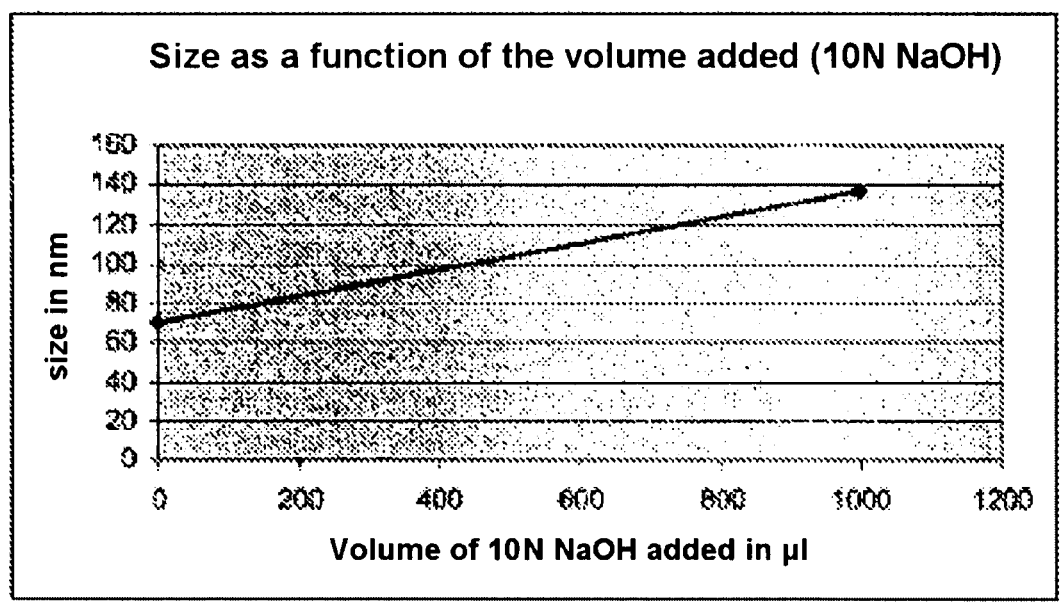

FIG. 2: Change in the size (in nm) of the nanocapsules obtained according to the preparation method of the invention, as a function of the volume of NaOH (10N) added (in µl), in the presence of a constant amount of human serum albumin.

Figure 3:
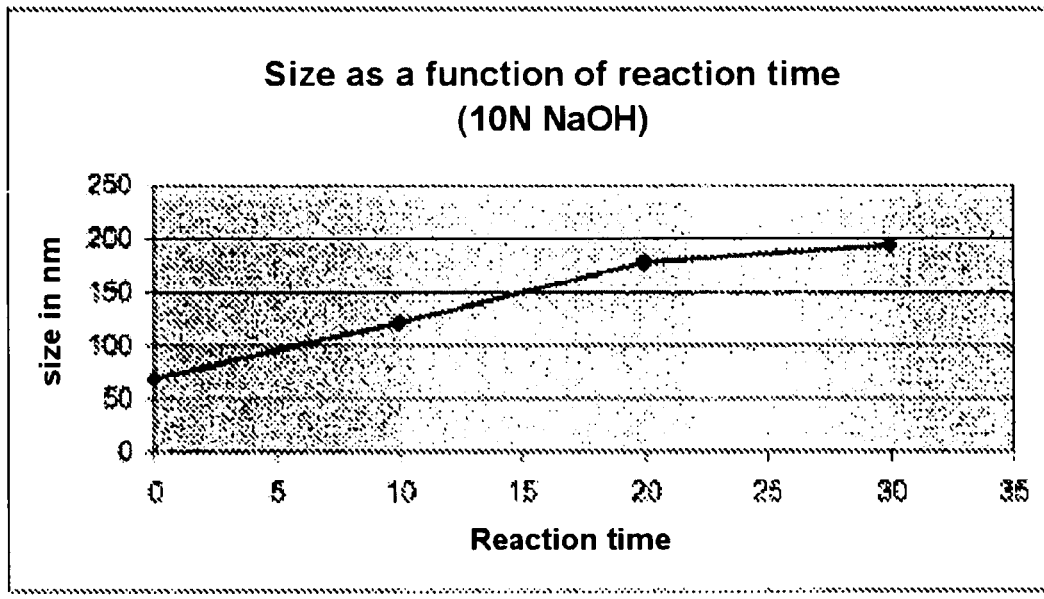

FIG. 3: Change in the size (in nm) of the nanocapsules obtained according to the preparation method of the invention, as a function of the reaction time and for a fixed volume of NaOH (10N) of 500 µl, in the presence of a constant amount of human serum albumin.

Figure 4:
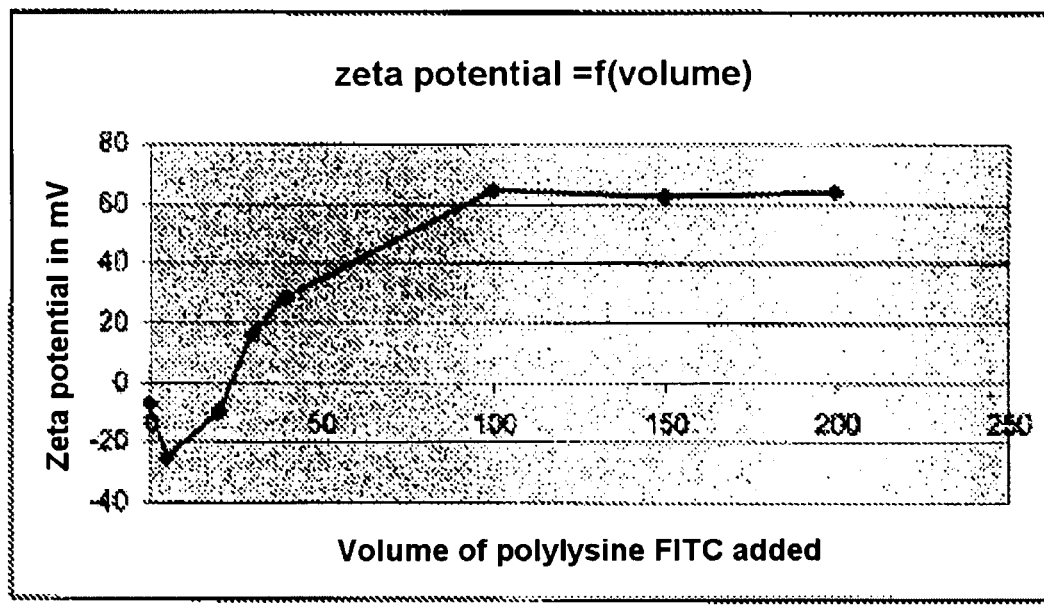

FIG. 4: Change in the zeta potential (in mV) of the nanocapsules obtained according to the preparation method of the invention, as a function of the volume of polylysine added (in µl).

Figure 5:
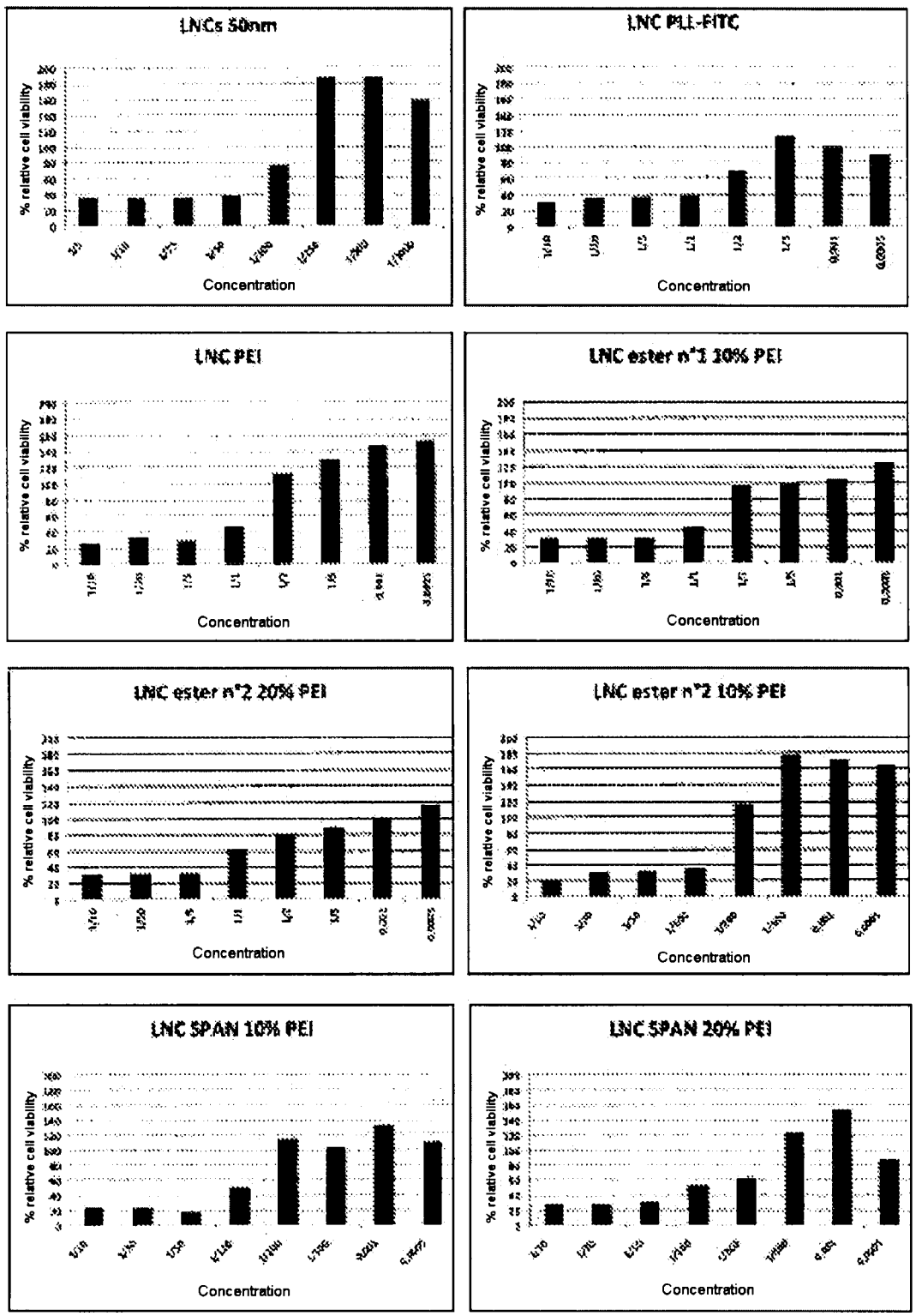

FIG. 5: Change in the relative cell viability (as %) on a cell line U87MG as a function of the concentration of nanocapsules, modified or nonmodified, obtained according to the preparation method of the invention.

Figure 6:
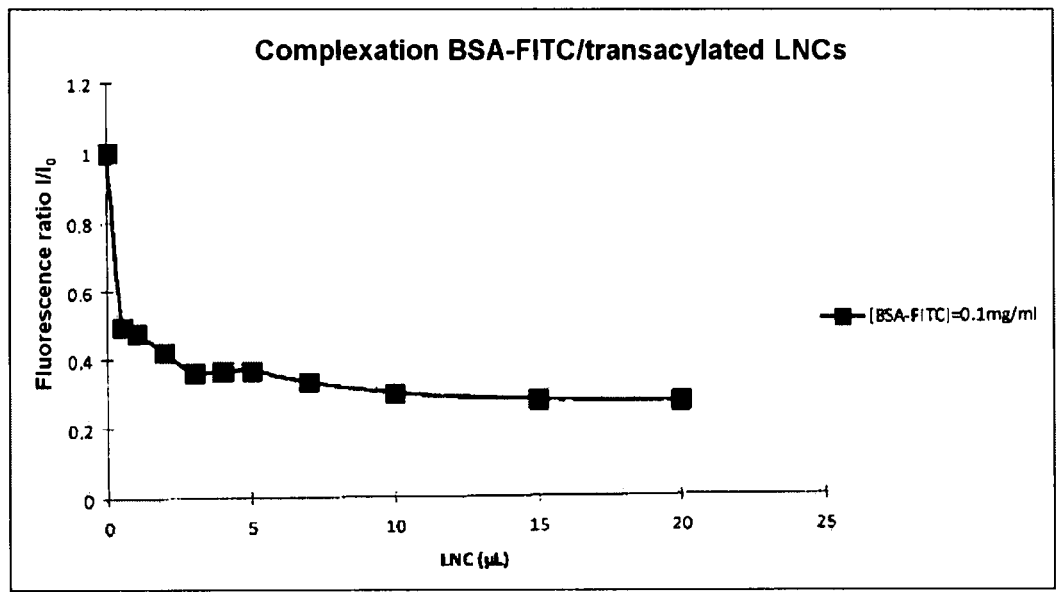

FIG. 6: Change in the $I/I_0$ ratio as a function of the concentration of LNCs modified by transacylation, I representing the fluorescence intensity of BSA-FITC fluorescent complexes adsorbed onto these LNCs, while $I_0$ represents the fluorescence intensity of the free BSA-FITC in solution.

Figure 7:
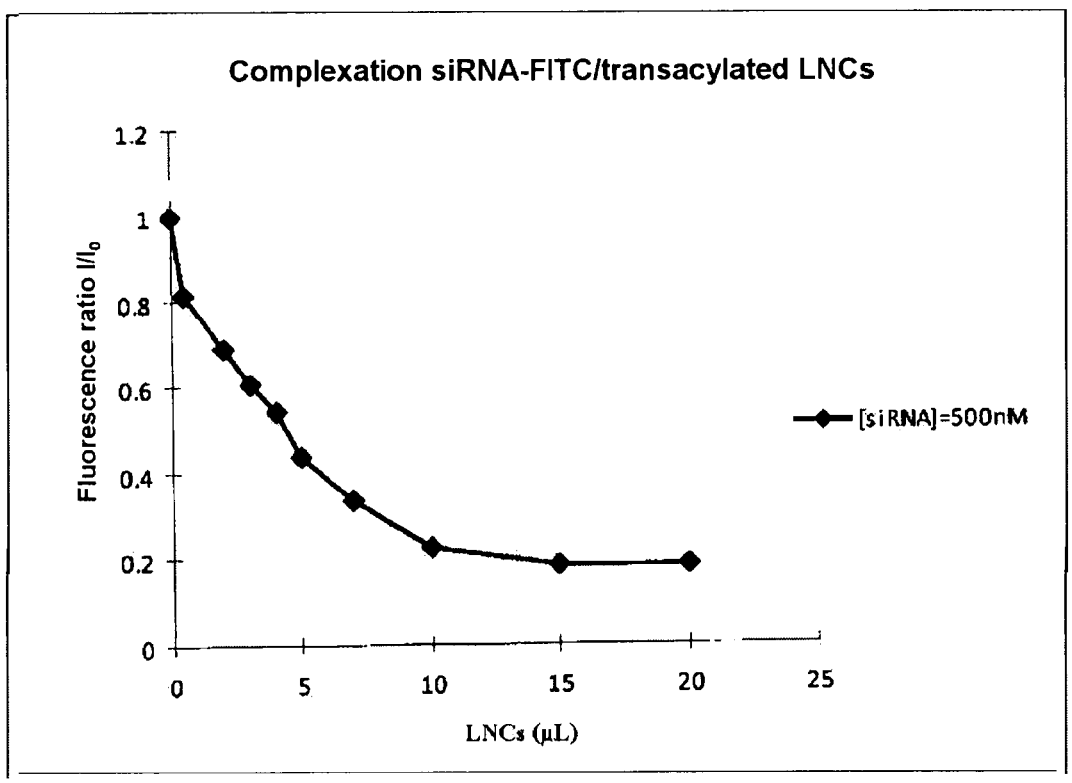

FIG. 7: Change in the $I/I_0$ ratio as a function of the concentration of LNCs modified by transacylation, I representing the fluorescence intensity of fluorescent siRNA-FITCs complexes adsorbed onto these LNCs, while $I_0$ represents the fluorescence intensity of the siRNA-FITCs free in solution.

EXAMPLE 1

Preparation of Nanocapsules Functionalized with Human Serum Albumin

1. Preparation of a Microemulsion not Loaded with Active Agent 5 g of an emulsion containing 75 mg of Lipoid S75-3®, 504 mg of lipophilic Labrafac WL 1349®, 504 mg of Solutol HS®, 15.383 g of water and 88 mg of sodium chloride are prepared.

The whole is combined in the same beaker and stirred magnetically. It is heated until a temperature of 85° C. is reached. Still with magnetic stirring, the system is allowed to cool to a temperature of 60° C. These thermal cycles (between 85° C. and 60° C.) are carried out three times so as to obtain increasingly structured microemulsions. The system is then held in its microemulsion form by stabilizing it at a temperature included in (or in close proximity to) the phase inversion zone, in this case 65° C.

2. Obtaining of LNCs

The microemulsion stabilized at the phase inversion temperature is cooled either abruptly or diluted with cold water so as to form a suspension of LNCs.

3. Binding of Human Serum Albumin 10 ml of "LNC" nanocapsules are incubated for 10 minutes, with stirring, in the presence of NaOH (1N) (varying volume from 0 to 2000 µl). Next, 500 µl of a solution of human serum albumin at 5% by weight are added. The mixture is left to react for 15 minutes, and then the solution is neutralized with a solution of hydrochloric acid having a concentration of 1 M, the volume depending on the volume of sodium hydroxide used at the start. The results obtained are indicated in FIG. 1.

EXAMPLE 2

Preparation of Nanocapsules Functionalized with Human Serum Albumin

The functionalized LNCs are prepared by analogy with the method described in example 1, this time using a solution of NaOH (10N).

The results obtained are indicated in FIG. 2.

EXAMPLE 3

Preparation of Nanocapsules Functionalized with Human Serum Albumin

The functionalized LNCs are prepared by analogy with the method described in example 2, this time varying the reaction time from 0 to 30 minutes.

The results obtained are indicated in FIG. 3.

EXAMPLE 4

Preparation of Nanocapsules Functionalized with Polylysine FITC

The preparation is carried out by analogy with the method of preparation of example 1, this time varying the volume of polylysine added from 0 to 200 µl. The zeta potential is measured as a function of the volume of polylysine added.

The results obtained are indicated in FIG. 4.

It is very clearly apparent that there is a dependency between the zeta potential of the modified lipid nanocapsules and the amount of polylysine introduced into the reaction mixture, i.e. a relationship between the amount of polylysine bound to the lipid nanocapsules and the zeta potential of the latter, which conditions their ability to bind negatively charged hydrophilic molecules.

Furthermore, it is possible to follow, over the course of the production steps, the amount of proteins bound to the lipid nanocapsules.

Table I below gives the results of assaying the proteins before and after the dialysis step. The assay is based on the µBCA method.

µBCA is a spectrophotometric assay method based on the absorption of light by a complex formed by the proteins to be assayed and the µBCA reagent. This method requires the use of a calibration range prepared from a solution of proteins of known concentration (µBCA from PIERCE).

TABLE I

| Sample No. | Protein concentration before dialysis in µg per ml | Sample No. | Protein concentration after dialysis in µg per ml |
|---|---|---|---|
| 1 | 184.28 | 1 | 310 |
| 2 | 371.42 | 2 | 281.42 |
| 3 | 601.42 | 3 | 448.57 |
| 4 | 642.85 | 4 | 622.85 |
| 5 | 1228.57 | 5 | 530 |
| 6 | 1002.85 | 6 | 504.28 |
| 7 | 1274.28 | 7 | 982.85 |

EXAMPLE 5

Use of Nanocapsules Functionalized with Polylysine FITC for siRNA Complexation The nanocapsules functionalized with polylysine FITC are prepared by analogy with the method of preparation of example 1, in the presence of 0.5 µl of LNCs of 50 nm and 400 µl of PLL-FITC. The whole is dialyzed and filtered and its pH is adjusted to 7.4.

These particles functionalized with polylysine FITC are then brought into contact with various volumes (2, 3, 4, 5, 6, 7, 8, 9, 10, 12, 15 and 20 µl) of siRNA (20 bp, i.e. 16 000 Daltons) having a concentration of 0.001 µmol/ml.

All of the mixtures thus prepared are characterized on an electrophoretic gel.

For comparative purposes, the siRNA alone, and a representative low-molecular-weight 20 bp PCR standard are also run on an electrophoretic gel.

It is noted that, for all the mixtures formed from, respectively, 2 µl to 15 µl of the siRNA solution, a single spot appears on the electrophoretic gel, corresponding to the siRNA complexed.

On the other hand, beyond 15 µl, only a partial complexation of the siRNA is now observed. It therefore appears that, beyond 15 µl of siRNA (0.001 µmol/ml), the binding capacity of the LNCs is exceeded.

EXAMPLE 6

Preparation of Nanocapsules Functionalized with Alcohol Esters

1) Ester Synthesis

Two alcohol esters, ester 1 and ester 2, were synthesized and have the following chemical structures:

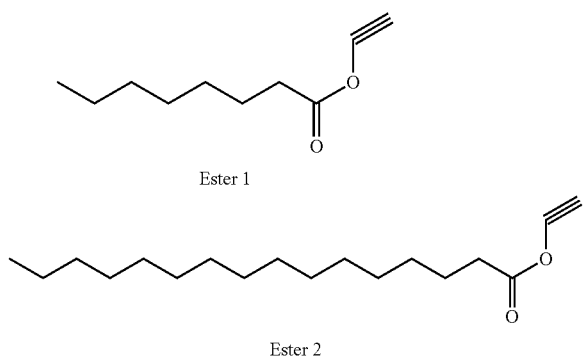

Ester 1

Ester 2

These two esters are synthesized according to the following protocol.

0.1 mol, respectively, of octanoyl chloride (ref. O4733, Sigma-Aldrich) or of palmitoyl chloride (ref. P78, Sigma-Aldrich) is first introduced into a 250 ml three-necked round-bottomed flask, followed by 150 ml of diethyl ether (ref. 346136, Sigma-Aldrich). After magnetic stirring, the mixture is cooled using a bath of ice-cold water, before the successive introduction of 0.15 mol of alcohol and then 0.15 mol of triethylamine (ref. T0886, Sigma-Aldrich).

After removal from the bath of ice-cold water, the mixture is brought to reflux for 2 hours.

After interruption of the heating and cooling, the reaction mixture is filtered through filter paper before a liquid-liquid extraction with dichloromethane (ref. 443484, Sigma-Aldrich) is carried out.

The organic phase is washed successively with water (twice 500 ml) and then a saturated solution of sodium chloride. The organic phase is then dried using anhydrous sodium sulfate, and then placed under reduced pressure in order to evaporate off the solvents.

The desired product is obtained in the form of a colorless liquid (ester 1) or of a white crystalline solid (ester 2). After drying of the product under reduced pressure, said product is weighed and the yield of the reaction is calculated.

Said yield is between 90 and 95%.

2) Obtaining of Ester-Loaded LNCs

Nanocapsules not loaded with active agents were obtained by means of the method described in example 1, the emulsion also this time comprising an amount of ester 1, of ester 2 or of Span 40® of 10 to 20% by weight of the amount of surfactants present in the emulsion (Solutol HS-15 and Lipoid S75-3).

Span 40® (ref 85545, Fluka) is an ester having the following formula:

3) Binding of Human Serum Albumin

The LNCs are functionalized according to the protocol described in example 1.

4) Results

The physicochemical characteristics of the lipid nanocapsules thus produced are reported in table II below:

TABLE II

| Sample name | Hydrodynamic diameter in nm (*) | zeta potential in mV (**) |
|---|---|---|
| LNCs 50 nm + 10% ester 2 | 30.1 | −15 |
| LNCs 50 nm + 10% ester 2 | 32 | −12 |
| LNCs 50 nm + 20% ester 2 transacylation PEI | 40.1 | 25.5 |
| LNCs 50 nm + 20% ester 2 transacylation PEI | 44.1 | 37.3 |
| LNCs 50 nm + 10% ester 1 | 31.3 | −23.9 |
| LNCs 50 nm + 20% ester 1 | 35.2 | −29.3 |
| LNCs 50 nm + 10% ester 1 transacylation PEI | 52 | 34.3 |
| LNCs 50 nm + 20% ester 1 transacylation PEI | 54.5 | 38.7 |
| LNCs 50 nm + 10% Span 40 | 52 | −7 |
| LNCs 50 nm + 20% Span 40 | 85 | 42 |
| LNCs 50 nm + 10% Span 40 transacylation PEI | 48 | −4 |
| LNCs 50 nm + 20% Span 40 transacylation PEI | 90.2 | 24.8 |

(*) and (**): these values were measured using a NanoZS (Malvern Instruments).

EXAMPLE 7

Measurement of the Transacylation Yield in the Presence of Esters

After purification, the transacylation reactants were assayed in order to visualize the increase in the transacylation yield linked to the use of the esters mentioned above.

The assay method is based on the use of o-phthaldialdehyde (OPA) as reactant, and takes place according to the following empirical equation:

The indole derivatives produced are fluorescent and make it possible to quantify the total primary amine groups present in the sample of nanocapsules.

First of all, a calibration range of the substance to be assayed is prepared. To do this, the substance is dissolved at various concentrations (50, 100, 150 and 200 µg/ml) in water at pH 7.4. The fluorescence of these solutions is evaluated at 460 nm, for an excitation wavelength of 355 nm.

The substance of interest is then assayed in the lipid nanocapsule samples by adding 300 µl of OPA to 30 µl of LNC solution.

The fluorescence of this solution is measured at 460 nm and the concentration of substance is calculated using the calibration range.

This assay method was used successfully to assay the reactant grafted onto the lipid nanocapsules during the transacylation step. For each reactant (poly-L-lysine (PLL) and polyethyleneimine (PEI)), a specific calibration range was used. The results of the assay, carried out after purification of the sample, are reported in table III below:

TABLE III

| Sample name | Polymer concentration µg/ml | % binding yield |
|---|---|---|
| LNCs 50 nm transacylation poly-L-lysine | 0.98 | 0.98 |
| LNCs 50 nm + 10% ester 1 transacylation PEI | 15 | 15 |
| LNCs 50 nm + 20% ester 1 transacylation PEI | 23 | 23 |
| LNCs 50 nm + 10% ester 2 transacylation PEI | ND | ND |
| LNCs 50 nm + 20% ester 2 transacylation PEI | 1.6 | 1.6 |
| LNCs 50 nm + 10% Span 40 transacylation PEI | 1.06 | 1.06 |
| LNCs 50 nm + 20% Span 40 transacylation PEI | 2.53 | 2.53 |

The binding yield corresponds to the ratio of the amount of substance grafted onto the LNCs (CR) to the maximum theoretical amount of this substance (CT).

The grafted substance is assayed via the OPA method in order to obtain the CR. The binding yield R can then be written as:

$R=(CR/CT)\times 100$

As can be observed in this table, when the trans-acylation reaction is produced on conventional lipid nanocapsules (LNCs 50 nm transacylation poly-L-lysine), the binding yield is close to 1%.

The introduction of 10 or 20% of ester 2 or of Span 40 into the formulation makes it possible to multiply this yield by a factor of between 2 and 3.

The introduction of 10 or 200 of ester 1 into the formulation leads, for its part, to an increase in the yield by a factor of between 15 and 25.

EXAMPLE 8

Evaluation of the Toxicity of the Nanocapsules Obtained by the Transacylation Method The toxicity of the lipid nanocapsules modified via the transacylation method was evaluated using the MTT (3-(4,5-dimethylthiazol-2-yl)-2,5-diphenyltetrazolium bromide) test.

This test aims to measure the toxicity of the nanoparticles by measuring the relative viability of the cells exposed to the nanoparticles, with cells not treated with nanoparticles being taken as control.

The tetrazolium ring contained by the MTT reactant is reduced to formazan by mitochondrial succinate dehydrogenase of active living cells.

The color of the medium then changes from yellow to purplish-blue, the strength of this coloration being proportional to the number of living cells present during the test, but also to their metabolic activity.

For this test, reference may be made to the tests described in the documents "Mosmann T., *Journal of immunological methods* 65 (1-2): 55-63, December 1983" and "Cory et al., *Cancer communications* 3 (7): 207-12, July 1991".

This test was carried out on a human tumor cell line, U87MG cells (HTB-14, LGC standard).

In order to ensure good statistical significance of the test, each assay was carried out in quintuplicate.

The results obtained are indicated in FIG. 5.

For each graph, the relative cell viability is expressed as a function of the concentration of the modified or nonmodified nanocapsules. U87MG cells not treated with nanoparticles are used as a reference. The value obtained with these cells represents a cell viability of 100%.

It can be observed that, in general, the nanocapsules modified during the transacylation step exhibit toxicity profiles comparable to the profile of the starting nanocapsules.

In the light of the results obtained, the grafting of natural or synthetic polymers does not cause any additional toxicity.

Indeed, it was observed that the nanocapsules obtained by transacylation show no toxicity for concentrations less than 1/300 of the initial suspension.

EXAMPLE 9

Development of Multilayer Structures Around Lipid Nanocapsules Modified by Transacylation A transacylation is carried out, at 25° C. using 40 µl of a 5% solution of poly-L-lysine (PLL), for 15 minutes, on 2 ml of a suspension of 50 nm LNCs obtained according to the method described in example 1. The mixture is then neutralized by the addition of 2 ml of a 0.5M glycine buffer at pH 2.2.

After dialysis against milliQ water, 50 µl of trans-acylated LNCs are brought into contact with 0.045 nano-mol of siRNA, and then diluted with 2.95 ml of milliQ water. All of the siRNAs then bind to the LNCs. The siRNA concentration is 15 nanomol per liter.

This results in an increase in the hydrodynamic diameter of the particles, and also an inversion of their zeta potential, thus confirming the adsorption of the siRNAs onto the LNCs.

A layer of polymers (poly-L-lysine) is subsequently adsorbed onto the LNCs according to the following protocol.

5 µl of the 5% polylysine solution are added to the suspension of LNCs-siRNA so as to form LNCs-siRNA-PLL systems, which can then be purified by dialysis against a 10 mM NaCl solution.

The resulting LNCs have a positive zeta potential, thus attesting to the adsorption of the polymer in a multi-layer structure.

EXAMPLE 10

Binding of Model Proteins to Nanocapsules Modified by Transacylation

This study consists of the adsorption of fluorescent proteins or nucleic acids onto the modified LNCs.

1) BSA-FITC Fluorescent Protein

Experiments were carried out with BSA-FITC at various concentrations: 0.5 mg/ml, 0.33 mg/ml, 0.25 mg/ml, 0.2 mg/ml and 0.1 mg/ml.

These FITC-labeled proteins were obtained according to the following protocol.

900 µl of a solution of BSA at 2.77 mg/ml in 0.1M sodium bicarbonate at pH 9 are mixed with 250 µl of a solution of FITC at 4 mg/ml in dimethyl sulfoxide, the reaction being left to stir in the dark at 25° C. for 2 hours. The labeled proteins are then separated from the FITC that has not reacted, by size exclusion chromatography on Sephadex G-25® gel.

The amount of protein and also the amount of FITC bound to the proteins are then assayed according to the following protocol.

A BSA calibration range and an FITC calibration range are prepared in 5 mM PBS, the absorbance being measured at 280 nm for BSA and at 490 nm for FITC.

The aborbances at 280 nm and 490 nm of the solution of labeled proteins are then measured and compared with the calibration ranges in order to determine the respective concentrations of BSA and of FITC. The ratio of the FITC concentration to the BSA concentration can then be calculated.

The step of complexation between transacylated LNCs and fluorescent proteins is then carried out according to the following protocol.

In order to obtain the $I_0$ fluorescence values, the fluorescence and fluorescence intensities of solutions of BSA-FITC with known concentrations are measured. The same solutions of BSA-FITC are then prepared in the presence of increasing concentrations of transacylated nanocapsules. The fluorescences and fluorescence intensities of these solutions are then also measured (I).

When the $(I-I_0)/I_0$ ratio is compared for each concentration of modified LNCs, a decrease in the fluorescence intensity as the concentration of modified LNCs increases is observed.

The fluorescence measurement results obtained are represented in FIG. 6.

When similar experiments were carried out with LNCs not pre-transacylated, no variation in fluorescence intensity was observed.

2) siRNA-FITC

The same experiments were carried out with siRNA-FITCs in place of the BSA-FITC. The same decrease in fluorescence intensity as the concentration of modified LNCs increases is observed.

The fluorescence measurement results obtained with the siRNA-FITCs are represented in FIG. 7.

The invention claimed is:

1. A capsule, comprising:
a liquid lipid core; and
a solid lipid shell surface-functionalized with at least one compound (a) comprising at least one amine functional group
wherein a shell architecture of the liquid lipid core and the solid lipid shell is on the nanometric scale, and
wherein the at least one compound (a) is covalently bonded to a surface of the solid lipid shell via a transacylation reaction.

2. The capsule of claim 1, wherein at least one compound (a) covalently bonded to the surface of the solid lipid shell is covalently bonded to a molecule of interest (b).

3. The capsule of claim 2, wherein at least one selected from the group consisting of the at least one compound (a) and the molecule of interest (b) is a protein, a peptide, a nucleic acid, a polymer, an inorganic, or an organometallic.

4. The capsule of claim 1, wherein the at least one compound (a) is at least one protein selected from the group consisting of an albumin, a gelatin, and a polypeptide.

5. The capsule of claim 2, wherein at least one selected from the group consisting of the at least one compound (a) and the molecule of interest (b) is a nucleic acid molecule.

6. The capsule of claim 1, wherein the solid lipid shell comprises at least one liposoluble surfactant.

7. The capsule of claim 6, wherein the at least one liposoluble surfactant is at least one selected from the group consisting of a phospholipid, a lecithin and a phosphatidycholine.

8. The capsule of claim 1, wherein the solid lipid shell comprises at least one surfactant system comprising a lipophilic surfactant and a nonionic hydrophilic thermosensitive surfactant.

9. The capsule of claim 8, wherein the nonionic hydrophilic thermosensitive surfactant is at least one selected from the group consisting of a phospholipid, a polyethoxylated sorbitol fatty acid ester, an ester of a polyethylene glycol and a fatty acid, a polyethoxylated fatty acid, a polyoxyethylenated fatty alcohol ether, a polyoxyethylenated nonphenyl ether, a polyoxyethylenated hydroxyphenyl ether, and a polyethylene glycol 2-hydroxystearate.

10. The capsule of claim 1, wherein the solid lipid shell comprises at least one alcohol ester.

11. The capsule of claim 10, wherein the alcohol ester is at least one selected from the group consisting of an alcohol ester comprising a carbon number less than or equal to 12, wherein the carbon number is an integer.

12. The capsule of claim 10, wherein the at least one alcohol ester has the following formula:

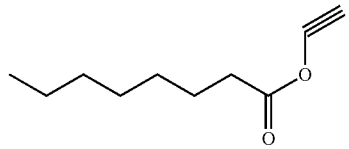

13. The capsule of claim 1, wherein the solid lipid shell comprises at least one liposoluble surfactant, and
wherein the transacylation reaction is between the at least one liposoluble surfactant and the at least one compound (a).

14. The capsule of claim 1, wherein the solid lipid shell comprises lecithin and wherein the at least one compound (a) is covalently bonded to the surface of the solid lipid shell via a transacylation reaction employing a lecithin.

15. The capsule of claim 1, wherein the solid lipid shell comprises at least one alcohol ester and wherein the transacylation reaction is between the at least one alcohol ester and the at least one compound (a).

16. The capsule of claim 1, wherein the liquid lipid core comprises at least one oily fatty phase comprising at least one liquid or semi-liquid fatty substance.

17. The capsule of claim 1, wherein the capsule encapsulates at least one selected from the group consisting of at least one active agent in the liquid lipid core and the solid lipid shell.

18. A method for the functionalization of nanocapsules, the method comprising:
ii) contacting nanocapsules comprising a solid lipid shell and a liquid lipid core with an alkaline aqueous solution, thereby activating a surface of the nanocapsules for a transacylation reaction and obtaining a medium;
iii) contacting the medium ii) with at least one compound (a) comprising at least one amine functional group, to obtain, by transacylation, the functionalized nanocapsules;
iv) optionally, neutralizing the functionalized, nanocapsules; and
v) optionally, isolating the functionalized nanocapsules.

19. The method of claim 18, wherein the at least one compound (a) is a protein, a peptide, a nucleic acid, a polymer, an inorganic, or an organometallic.

20. The method of claim 18, wherein the transacylation reaction implements an alkalinisation via a sodium hydroxide solution.

21. A capsule obtained by the method of claim 18.

22. The capsule of claim 1, wherein the capsule is suitable for use in a therapeutic, cosmetic or nutraceutical composition.

23. A composition, comprising:
the capsule of claim 1; and
at least one physiologically acceptable vehicle.

* * * * *